(12) United States Patent
Chang et al.

(10) Patent No.: US 12,110,310 B2
(45) Date of Patent: Oct. 8, 2024

(54) AMPHIPHILIC KANAMYCIN COMPOSITIONS AND METHODS

(71) Applicants: Cheng-Wei Tom Chang, Logan, UT (US); Jon Y Takemoto, North Logan, UT (US)

(72) Inventors: Cheng-Wei Tom Chang, Logan, UT (US); Jon Y Takemoto, North Logan, UT (US)

(73) Assignee: UTAH STATE UNIVERSITY, North Logan, UT (US)

( * ) Notice: Subject to any disclaimer, the term of this patent is extended or adjusted under 35 U.S.C. 154(b) by 190 days.

(21) Appl. No.: 17/157,752

(22) Filed: Jan. 25, 2021

(65) Prior Publication Data

US 2021/0230203 A1 Jul. 29, 2021

Related U.S. Application Data

(60) Provisional application No. 62/965,071, filed on Jan. 23, 2020.

(51) Int. Cl.
| | | |
|---|---|---|
| *C07H 15/23* | (2006.01) | |
| *A61K 31/7036* | (2006.01) | |
| *A61P 31/04* | (2006.01) | |
| *C07H 15/234* | (2006.01) | |

(52) U.S. Cl.
CPC ......... *C07H 15/23* (2013.01); *A61K 31/7036* (2013.01); *A61P 31/04* (2018.01); *C07H 15/234* (2013.01)

(58) Field of Classification Search
CPC .................................................... C07H 15/234
See application file for complete search history.

(56) References Cited

U.S. PATENT DOCUMENTS

| | | | | |
|---|---|---|---|---|
| 4,024,332 A | * | 5/1977 | Fenner ................ | C07H 15/234 536/13.6 |
| 4,493,831 A | * | 1/1985 | Takaya ................ | C07H 15/234 514/35 |
| 8,865,665 B2 | | 10/2014 | Chang | |
| 9,127,035 B2 | | 9/2015 | Auclair | |
| 9,260,464 B2 | | 2/2016 | Lake | |
| 9,469,863 B2 | | 10/2016 | Sumida | |
| 9,669,044 B2 | | 6/2017 | Takemoto | |
| 10,337,044 B2 | | 7/2019 | Yoon et al. | |
| 2011/0130357 A1 | | 6/2011 | Chang | |
| 2021/0163521 A1 | * | 6/2021 | Altenberg ............ | A61P 9/00 |

FOREIGN PATENT DOCUMENTS

| | | | |
|---|---|---|---|
| EP | 0009197 A1 | 4/1980 | |
| EP | 0107850 B1 | 5/1984 | |
| WO | WO-2019241347 A1 * | 12/2019 | ............... E05D 3/00 |

OTHER PUBLICATIONS

Carrer et al., "Kanamycin resistance as a selectable marker for plastid transformation in tobacco" Mol Gen Genet vol. 241 pp. 49-56 (Year: 1993).*
Nalage et al., "Kanamycin A 6'-pyrenylamide: a selective probe for heparin detection" Tetrahedron Letters vol. 53 pp. 2864-2867 (Year: 2012).*
Matsuda et al., "Studies On Antiviral Agents IV. Synthesis and in Vitro Antiviral Activity of New N-Palmitoylkanamycin A" The Journal of Antibiotics vol. 39 No. 10 pp. 1479-1482 (Year: 1986).*
Aminova et al., "Two-Dimensional Combinatorial Screening Identifies Specific 6'-Acylated Kanamycin A- and 6'-Acylated Neamine-RNA Hairpin Interactions" Biochemistry vol. 47 pp. 12670-12679 DOI 10.1021/bi8012615 (Year: 2008).*
Marichev et al, "Highly selective acylation of polyamines and aminoglycosides by 5-acyl-5-phenyl-1,5-dihydro-4H-pyrazol-4-ones" Chem Sci vol. 8 pp. 7152-7159 DOI: 10.1039/c7sc03184j (Year: 2017).*
Chang et al., "Development of Fungal Selective Amphiphilic Kanamycin: Cost-Effective Synthesis and Use of Fluorescent Analogs for Mode of Action Investigation", ACS Infect. Dis., 2019, 473-483, vol. 5.
Chandrika et al., "Synthesis and Biological Activity of. Mono- and Di-N-acylated Aminoglycosides", ACS Med. Chem., Sep. 30, 2015, 1134-1139, Lett. 6.
Subedi et al., "Development of Fungal Selective Amphiphilic Kanamycin: Cost Effective Synthesis and Use of Fluorescent Analogs for Mode of Action Investigation", ACS Infectious Diseases 2019, Jan. 23, 2019, 473-483, 5.

* cited by examiner

*Primary Examiner* — Eric Olson
(74) *Attorney, Agent, or Firm* — Ryan L. Marshall; Barnes & Thornburg LLP

(57) ABSTRACT

The present relates to novel bioactive amphiphilic kanamycin compounds having the general formula of:

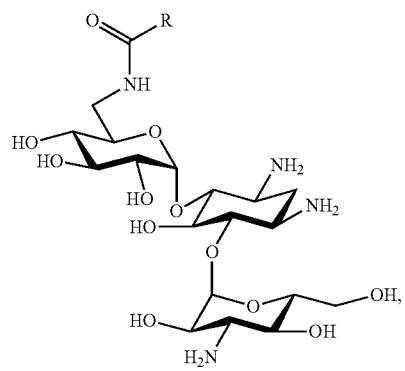

where R may be a $C_4$ to $C_{20}$ branched or straight chained alkyl group or a substituted or unsubstituted aryl group. Also provided are methods of synthesizing and methods of using the compounds of the present invention. The compounds of the present invention are useful in treating and preventing various fungal and bacterial diseases.

6 Claims, No Drawings

AMPHIPHILIC KANAMYCIN COMPOSITIONS AND METHODS

RELATED APPLICATIONS

This application claims priority to U.S. Provisional Application No. 62/965,071, filed on Jan. 23, 2020, which is hereby incorporated by reference in its entirety.

GOVERNMENT SPONSORED RESEARCH

This invention was made with government support under the following grants: (1) National Science Foundation, Division of Industrial Innovation and Partnerships Grant #STTR 1521060 and (2) US Department of Agriculture, NIFA, Utah Agriculture Experiment Station Grant #1017. The government has certain rights in the invention.

TECHNICAL FIELD

The present disclosure relates to active chemical compounds. More particularly, the present disclosure relates to amphiphilic kanamycin compounds, their antibiotic activities, and associated methods.

BACKGROUND

Aminoglycoside antibiotics (shown below), once effective against infectious bacterial infections, are plagued with the rampage of antibiotic resistant bacteria. See Subedi et al., Development of Fungal Selective Amphiphilic Kanamycin: Cost Effective Synthesis and Use of Fluorescent Analogs for Mode of Action Investigation, ACS Infectious Diseases 2019, 5 473-483 (Jan. 23, 2019) ("Subedi et al."). Subedi et al. was authored by some of the inventors of the instant application and is incorporated by reference in its entirety.

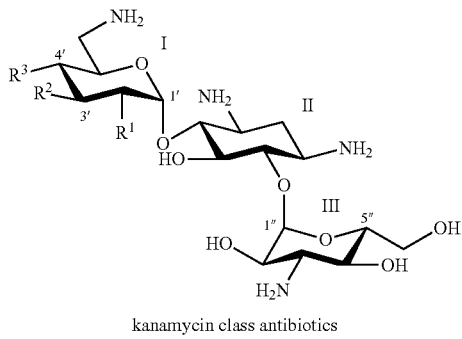

kanamycin class antibiotics

|  | $R^1$ | $R^2$ | $R^3$ |
|---|---|---|---|
| Kanamycin A | OH | OH | OH |
| Kanamycin B | OH | $NH_2$ | OH |
| Dibekacin | $NH_2$ | H | H |
| Tobramycin | $NH_2$ | H | OH |

Amphiphilic aminoglycosides provide a new strategy and approach in the fight against resistant microbes. See id. Unlike traditional aminoglycosides, amphiphilic aminoglycosides have been shown to increase the membrane permeabilities for both bacteria and fungi. See id. The antifungal activity of amphiphilic kanamycin ("AK") is of particular interest as it represents a new strategy of repurposing and reviving the use of an old drug.

To provide cost-effective antimicrobials, low-cost syntheses of AK for uses in green agriculture and human medicine were developed. K20 (shown below) displayed effectiveness in controlling *Fusarium* head blight in wheat field trials. See U.S. Pat. No. 8,865,665, incorporated by reference in its entirety. In addition, combinations of K20 and half-label rates of commonly employed agrofungicides significantly lowered deoxynivalenol (DON) mycotoxin levels in harvested grain. See U.S. Pat. No. 9,669,044, incorporated by reference in its entirety. Nevertheless, two shortcomings are associated with K20. First, the cost of production of K20 is not compatible with agrofungicides currently used in the market. Second, K20 contains a nonnatural structural scaffold that makes it difficult to be classified as a natural or organic fungicide. Also, questions still linger regarding the antifungal mode of action of the AKs. Several reports have shown that AKs increase the permeability of fungal membranes. However, it is unclear whether this is the sole mode of action (MOA) against fungi. Several studies have reported AKs that are active against both fungi and bacteria (nonfungal specific) while K20 and FG08 (shown below) is active only against fungi. See US Patent Application Publication No. 2011-0130357, incorporated by reference in its entirety. Therefore, it is of interest to determine the factors that cause AKs to be fungal or nonfungal specific agents.

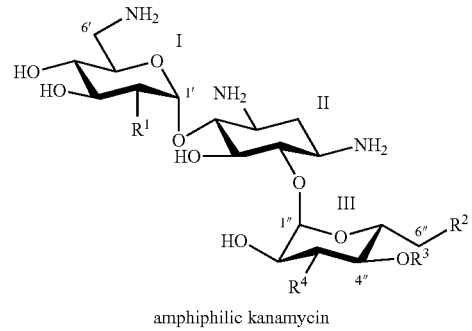

amphiphilic kanamycin

|  | $R^1$ | $R^2$ | $R^3$ | $R^4$ |
|---|---|---|---|---|
| K20 | OH | $OS(O)_2C_8H_{17}$ | H | $NH_2$ |
| FG08 | $NH_2$ | H | $C_8H_{17}$ | OH |

DETAILED DESCRIPTION

In the following description, numerous specific details are provided for a thorough understanding of specific preferred embodiments. However, those skilled in the art will recognize that embodiments can be practiced without one or more of the specific details, or with other methods, components, materials, etc. In some cases, well-known structures, materials, or operations are not shown or described in detail in order to avoid obscuring aspects of the preferred embodiments. Furthermore, the described features, structures, or characteristics may be combined in any suitable manner in a variety of alternative embodiments. Thus, the following more detailed description of the embodiments of the present invention, as illustrated in some aspects in the drawings, is not intended to limit the scope of the invention, but is merely representative of the various embodiments of the invention.

In this specification and the claims that follow, singular forms such as "a," "an," and "the" include plural forms unless the content clearly dictates otherwise. All ranges disclosed herein include, unless specifically indicated, all endpoints and intermediate values. In addition, "optional" or "optionally" refer, for example, to instances in which subsequently described circumstance may or may not occur, and include instances in which the circumstance occurs and instances in which the circumstance does not occur. The terms "one or more" and "at least one" refer, for example, to instances in which one of the subsequently described circumstances occurs, and to instances in which more than one of the subsequently described circumstances occurs.

Some or all of the following definitions may also be utilized throughout this disclosure.

Fungal Infection: The term "fungal infection" is defined herein as an association of a fungal organism with a host, whether said association is actual or potential. For example, an actual association occurs when a fungus is physically present on or within a host. Examples of potential associations include fungi on or within the environment surrounding a host, where the fungi are at least somewhat likely to be actively or passively transferred to the host. Without wishing to further limit the type of associations between a fungal organism and host, examples of the association of the fungal organism with the host include biological associations that may be pathogenic or non-pathogenic, parasitic or non-parasitic, symbiotic or non-symbiotic, mutualistic or non-mutualistic, commensal, naturally occurring or man-made, or any other biological interaction.

Bacterial Infection: The term "bacterial infection" is defined herein as an association of a bacterial organism with a host, whether said association is actual or potential. For example, an actual associate occurs when bacteria are physically present on or within a host. Examples of potential associations include bacteria on or within the environment surrounding a host, where the bacteria are at least somewhat likely to be actively or passively transferred to the host. Without wishing to further limit the type of associations between a bacterial organism and host, examples of the association of the bacterial organism with the host include biological associations that may be pathogenic or non-pathogenic, parasitic or non-parasitic, symbiotic or non-symbiotic, mutualistic or non-mutualistic, commensal, naturally occurring or man-made, or any other biological interaction.

Host in need thereof: The phrase "host in need thereof" is defined herein as any host associated or potentially associated with a fungal organism, where said host may actually or potentially benefit from elimination, prevention, or alleviation of a fungal infection.

*Fusarium* Head Blight: The phrase "*Fusarium* head blight" is defined herein as any fungal disease caused by the fungus *Fusarium graminearum*.

Surfactant: The term "surfactant" is used to indicate the common laboratory surfactant $C_{58}H_{114}O_{26}$. All uses of the term "surfactant" refer to $C_{58}H_{114}O_{26}$, unless otherwise indicated.

Prophylactically: The term "prophylactically" is used herein to refer to the administration of an antimicrobial compound for the prevention of disease.

N/A: As used herein to describe data points, the abbreviation "N/A" means not tested.

Adjuvant: The term "adjuvant" is defined herein as a substance that helps and enhances the pharmacological effect of a drug or increases the ability of an antigen to stimulate the immune system.

Excipient: The term "excipient" is defined herein as an inactive substance used as a carrier for the active ingredients of a medication.

Diluent: The term "diluent" is defined herein as any liquid or solid material used to dilute or carry an active ingredient.

Antifungal amount or antifungal effective: Unless otherwise specified, the phrases "antifungal amount" or "antifungal effective" are used herein to describe an amount of an antifungal agent sufficient to reduce, eliminate, or alleviate a fungal infection or the symptoms of a fungal infection on or within a host.

MIC: The term MIC means the minimal inhibitory concentration or lowest concentration of an antimicrobial that will inhibit the visible growth of a microorganism after 24, 48, or 72 hours of incubation.

Admixed: The term "admixed" is used herein to describe a chemical or compound in a mixture or combination with other chemicals or compounds.

Administering: The term "administering" is defined herein to describe the act of providing, exposing, treating, or in any way physically supplying or applying a chemical or compound to any living organism or inanimate object associated with a living organism, where said organism will actually or potentially benefit for exposure, treatment, supplying or applying of said chemical or compound.

Topical: The term "topical" is defined herein as pertaining to the surface of a body part, surface part of a plant, or surface of an inanimate object or composition, such as soil. For example, in medicine, a topical medication is applied to body surfaces such as the skin or mucous membranes, for example throat, eyes and ears.

Carrier: The term "carrier" is defined herein as any substance that serves to improve the delivery and the effectiveness of a drug or antimicrobial agent and is inclusive of excipients as defined above. Examples include: microspheres made of biodegradable polymer poly(lactic-co-glycolic) acid, albumin microspheres, synthetic polymers (soluble), protein-DNA complexes, protein conjugates, erythrocytes, nanoparticles, and liposomes Grain head: The phrase "grain head" as used herein is meant to include both small and large grains.

Warm-blooded animal: Used herein the phrase "warm-blooded animal" means an animal characterized by the maintaining of a relatively constant and warm body temperature independent of environmental temperature; homeothermic.

Certain terms in this application are to be interpreted as commonly used in the technical fields of medicine, antimicrobials, and crop disease, as indicated by the context of their use. These terms include spray nozzle, droplet, therapeutically, exterior, spraying, topical, treatment, and prevention.

The present disclosure covers compositions, methods of production, and methods of use for various AKs with the following general structure:

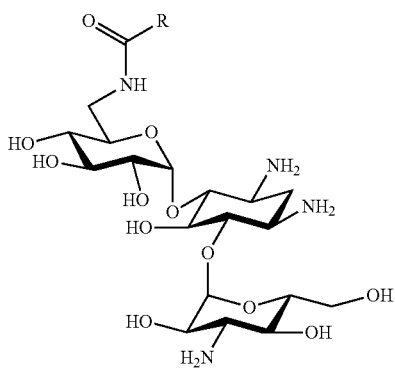

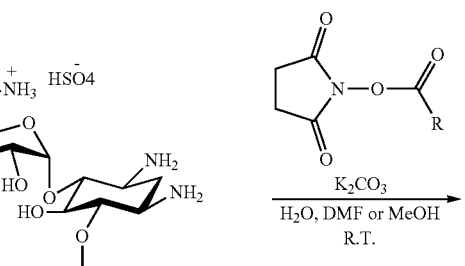

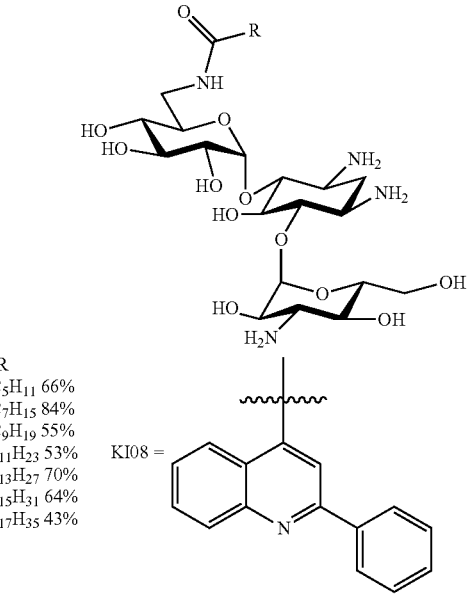

R may be selected from a $C_4$ to $C_{20}$ branched or straight chained alkyl group. For example, R may be one of the following alkyl groups: $C_5H_{11}$, $C_7H_{15}$, $C_9H_{19}$, $C_{11}H_{23}$, $C_{13}H_{27}$, $C_{15}H_{31}$, $C_{17}H_{35}$. Additionally, R may be an aryl group such as a substituted or unsubstituted phenyl, benzyl, naphthyl, anthracenyl, pyrenyl, or quinolinyl group. For example, R may be one of the following aryl groups:

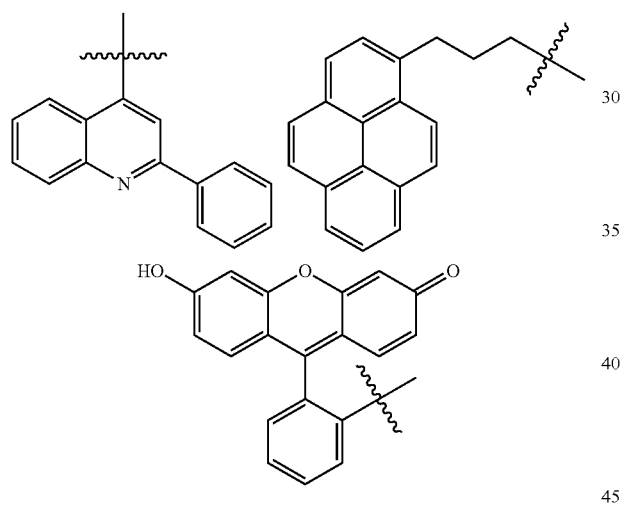

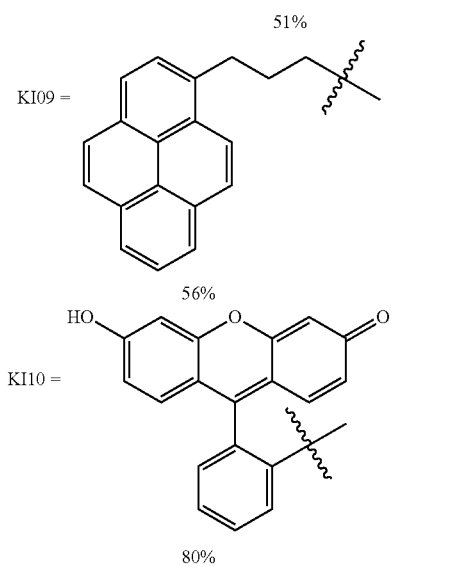

Production: The AKs were produced in a low-cost one-step modification of kanamycin. Kanamycin sulfate and fatty acids were used as the low-cost starting materials. One-step regioselective acylation of the amino groups on kanamycin A was undertaken. The fatty acids were converted into the corresponding esters of N-hydroxysuccinimide with modification of a previously reported method. See Chandrika, N. T., Green, K. D., Houghton, J. L., and Garneau-Tsodikova, S. (2015) Synthesis and Biological Activity of Mono- and Di-N-acylated Aminoglycosides. ACS Med. Chem. Lett. 6, 1134-1139. Slow addition of these esters to a solution of kanamycin A afforded the desired AKs (Scheme 1). Modest to excellent yields were achieved for the one-step regioselective acylation. On the basis of the chemicals needed, the cost of production of these AKs is about 1/10 of that for K20. Since both fatty acids and kanamycin are natural products, the newly synthesized AKs are anticipated to be classified as natural, thus meeting our goals of price competitiveness and natural and green products.

Biological Activity: The AK compounds, or salts thereof, may be administered to a host in need thereof in pharmaceutically appropriate amounts to treat and/or control fungal or bacterial infections. Exemplary hosts include humans, animals, and plants. Exemplary diseases for treatment include those caused by pathogens related to human, crop, or animal disease. In some embodiments, the AK compounds are administered in agricultural applications, such as to control fungal infections in banana cultivation, grain (e.g. wheat) cultivation, etc. In other embodiments, the AK compounds are administered to humans to control fungal and/or bacterial infections.

In further broad embodiments, the compound of the present invention is administered by spraying, direct injection, topical application, ingestion (including pharmaceutical compositions that include the structure related to the present invention), or by inclusion in the water supply, to either a human, an animal, or a crop immediately threatened by, or potentially threatened by, a pathogen, where the pathogen is causing or may cause fungal or bacterial disease(s), and administration of the compounds of the present invention will reduce, eliminate, or avoid the disease(s).

Exemplary fungal infections that may be treated with the AK compounds include those caused by *Fusarium graminearum*, such as *Fusarium graminearum* B4-5A; *Candida albicans*, such as *Candida albicans* 64124; *Cryptococcus neoformans*, such as *Cryptococcus neoformans* MYA2876; *Rhodotorula pilimanae; Candida parapsilosis, Candida Krusei, Candida aurus, Candida glabrata, Candida guillermondii, Paecilomyces variotii, Rhizopus arrhizus, Saksenaea species, Coccidioides species, Histoplasma capsulatum, Aspergillus fumigatus, Lomentospora prolificans, Scedosporium, Apophysomyces,* and *Blastomyces dermatitidis*.

Exemplary bacterial infections include those caused by *E. coli* and *S. aureus*, such as *E. coli* (ATCC 25922), *S. aureus* (ATCC 25923), *S. aureus* (ATCC 33591) MRSA, and *S. aureus* (ATCC 43300) MRSA.

ring containing at least one other non-carbon atom of either nitrogen, sulfur, or oxygen, such as azoles that include 1 nitrogen atom, 2 or more nitrogen atoms, 1 nitrogen atom and 1 oxygen atom, and 1 nitrogen atom and 1 sulfur atom. The five-membered nitrogen heterocyclic ring may be additionally substituted.

In some embodiments where the compounds are employed for biocidal or antibiotic effects, suitable azoles include those that have at least some desired biocidal effect. Exemplary azoles include pyrroles, pyrazoles, imidazoles, triazoles, tetrazoles, pentazoles, oxazoles, isoxazoles, thiazoles, and isothiazoles.

In some embodiments, the azole may be selected from one or more of the following: itraconazole, fluconazole, voriconazole, posaconazole, chlotrimazole, tioconazole, ketoconazole, metconazole, tebuconazole, and pyraclostrobin.

In embodiments, the azoles may be used as illustrated above, as salts, or any other suitable form for delivery to a target organism. For treatment of a fungal or fungal and bacterial infection, the ratio of azole to aminoglycoside may be from about 1:1 to about 1:1000, from about 1:5 to about 1:600, from about 1:20 to about 1:500, from about 1:30 to about 1:200, and from about 1:50 to about 1:100. For example, in some embodiments, the ratio of azole:aminoglycoside may be about 1:5, 1:21, 1:32, 1:53, 1:180, and 1:533.

Other exemplary antibiotics include other antifungal agents with mechanisms of inhibitory action that differ from that of the AK compounds.

Exemplary antifungal and antibacterial activities were determined for the compounds.

Antifungal activity for various compounds against a variety of exemplary fungal species is illustrated in Table 1.

TABLE 1

Minimum inhibitory concentrations of compounds against fungal strains[a]

| Compound | *Fusarium graminearum* B4-5A | *Candida albicans* 64124 | *Candida albicans* MYA2876 | *Cryptococcus neoformans* H99 | *Rhodotorula pilimanae* |
|---|---|---|---|---|---|
| KI01 | >256 | >256 | >256 | >256 | >256 |
| KI02 | >256 | >256 | >256 | >256 | >256 |
| KI03 | >256 | >256 | >256 | 128 | 128 |
| KI04 | 16 | 32 | 32 | 8 | 16 |
| KI05 | 8 | 16 | 16 | 4 | 4 |
| KI06 | 4 | 8 | 8 | 4 | 4 |
| KI07 | 4 | 8 | 8 | 4 | 4 |
| KI08 | >256 | >256 | >256 | 128 | 256 |
| KI09 | 16 | 16 | 16 | 16 | 16 |
| KI10 | 32 | 64 | 128 | 32 | 16 |
| K20 | 8 | 16 | 16 | 8 | 4 |
| Voriconazole | 32 | >256 | 0.125 | 0.125 | 8 |

[a]Unit: μg/mL

In some embodiments, the AK compounds are active against the following fungi: *C. parapsilosis, C. krusei. Paecilomyces variotii, C. auris, Aspergilla fumigatus, Lomentospora prolificans, Apophysomyces,* and *Blastomyces dermatitidis*; and against the following bacteria: Gram-negative bacteria, and Gram-positive bacteria.

The AK compounds may be administered in combination with other antibiotics. Suitable pharmaceutically active amounts may be used for AK compound and other antibiotics compound cocktails or combinations depending on the host and the infection being treated.

Exemplary antifungals include azoles. Azoles include compounds having a five-membered nitrogen heterocyclic Antifungal activity for various compounds against a variety of exemplary yeast species is illustrated in Table 2.

TABLE 2

Minimum inhibitory concentrations of compounds against yeast
YEAST

| | | KI06 | | KI07 | | Fluconazole |
|---|---|---|---|---|---|---|
| Species | Isolate No. | 50% | 100% | 50% | 100% | 50% |
| *C. parapsilosis* | ATCC 22019 | 4 | 8 | 4 | 4 | 1 |
| *C. krusei* | ATCC 6258 | 8 | 8 | 8 | 8 | 16 |

TABLE 2-continued

Minimum inhibitory concentrations of compounds against yeast
YEAST

| Species | Isolate No. | KI06 50% | KI06 100% | KI07 50% | KI07 100% | Fluconazole 50% |
|---|---|---|---|---|---|---|
| Candida auris | DI17-47 | 8 | 8 | 4 | 8 | >64 |
| | DI17-48 | 4 | 8 | 4 | 4 | 2 |
| | DI17-46 | 8 | 8 | 4 | 4 | >64 |
| | CAU1 | 4 | 8 | 4 | 8 | 2 |
| | CAU2 | 4 | 8 | 4 | 8 | 1 |
| | CAU3 | 4 | 8 | 4 | 8 | 0.5 |
| | CAU4 | 8 | 8 | 8 | 8 | >64 |
| | CAU5 | 8 | 8 | 4 | 8 | 16 |
| | CAU6 | 4 | 8 | 4 | 4 | 2 |
| | CAU7 | 4 | 8 | 4 | 4 | 2 |
| Candida glabrata | CG1 | 4 | 8 | 4 | 4 | >64 |
| | CG2 | 4 | 4 | 4 | 4 | 8 |
| | CG3 | 4 | 4 | 4 | 4 | 64 |
| Candida guillermondil | CGUI1 | 4 | 8 | 4 | 8 | 1 |
| | CGUI2 | 4 | 8 | 8 | 8 | 2 |
| | CGUI3 | 4 | 8 | 8 | 8 | 2 |
| Candida parapsilosis | CP1 | 4 | 8 | 8 | 8 | 0.5 |
| | CP2 | 4 | 8 | 8 | 8 | 0.5 |
| | CP3 | 8 | 16 | 8 | 8 | 0.5 |
| Cryptococcus neoformons | USC1597 | 4 | 4 | 4 | 4 | 2 |
| | H99 | 4 | 4 | 4 | 4 | 16 |
| | CN1 | 4 | 4 | 4 | 4 | 8 |

CLSI M27 & M38 methodologies were used to measure MICs
☐ All testing performed in RPMI buffered with 0.165M MOPS
☐ Concentration range for KI06, KI07, and Fluconazole: 0.125-64 mcg/ml
☐ Concentration range of Voriconazole and Posaconazole: 0.03-16 mcg/ml
☐ MICs at 24-72 hours
☐ Candida auris DI17-46 = isolate used in murine model
All values mcg/ml Antifungal activity for various compounds against a variety of exemplary filamentous and dimorphic fungi is illustrated in Table 3.

TABLE 3

Minimum inhibitory concentrations of compounds against fungal filamentous and dimorphic fungi
FILAMENTOUS & DIMORPHIC FUNGI

| Species | Isolate No. | KI06 50% | KI06 100% | KI07 50% | KI07 100% | Posaconazole 100% | Voriconazole 100% |
|---|---|---|---|---|---|---|---|
| P. variatil | MYA-3630 | 8 | 16 | 16 | 32 | ≤0.03 | 0.125 |
| Rhizopus arrhizus | 99-880 | 2 | 4 | 8 | 16 | 1 | — |
| | 99-892 | 2 | 4 | 8 | 16 | 0.25 | — |
| | RA1 | 2 | 4 | 4 | 8 | 0.25 | — |
| Saksenaeo sp. | SK1 | 1 | 1 | 4 | 4 | ≤0.03 | — |
| | SK2 | 1 | 2 | 2 | 2 | ≤0.03 | — |
| | SK3 | 1 | 2 | 1 | 4 | 0.125 | — |
| Coccidioldes sp. | Cocci1 | 4 | 8 | 8 | 8 | — | 0.25 |
| | Cocci2 | 4 | 8 | 8 | 16 | — | 2 |
| | DI17-143 | 4 | 8 | 8 | 8 | — | 0.125 |
| Histoplasma capsulatum | HC1 | 2 | 4 | 2 | 8 | — | 0.125 |
| | HC2 | 4 | 8 | ≤0.03 | ≤0.03 | — | ≤0.03 |
| | HC3 | 2 | 4 | | 8 | — | ≤0.03 |

CLSI M27 & M38 methodologies were used to measure MICs
☐ All testing performed in RPMI buffered with 0.165M MOPS
☐ Concentration range for KI06, KI07, and Fluconazole: 0.125-64 mcg/ml
☐ Concentration range of Voriconazole and Posaconazole: 0.03-16 mcg/ml
☐ MICs at 24-72 hours
☐ Candida auris DI17-46 = isolate used in murine model
All values mcg/ml Antifungal activity for various compounds against a various species is illustrated in Table 4.

TABLE 4

Minimum inhibitory concentrations of compounds against various species

| Species | Isolate | KI06 50% | KI06 100% | KI07 50% | KI07 100% | Fluconazole 50% | Voriconazole 100% | Pasaconazole 100% |
|---|---|---|---|---|---|---|---|---|
| C. parapsilosis | QC ATCC 22019 | 4 | 8 | 4 | 4 | 1 | — | — |
| C. krusei | QC ATCC 6258 | 4 | 8 | 4 | 8 | 16 | — | — |
| P. variotil | QC | 8 | 8 | 4 | 8 | — | 0.125 | ≤0.03 |
| C. albicans | CA1 | 4 | 4 | 4 | 4 | ≤0.125 | — | — |
| | CA2 | 4 | 8 | 4 | 8 | ≤0.125 | — | — |
| | CA3 | 2 | 4 | 4 | 4 | >64 | — | — |
| C. auris | DI17-47 | 2 | 4 | 0.25 | 0.5 | >64 | — | — |
| | DI17-48 | 1 | 4 | 0.25 | 0.5 | 2 | — | — |
| | DI17-46 | 4 | 8 | 0.5 | 1 | >64 | — | — |

TABLE 4-continued

Minimum inhibitory concentrations of compounds against various species

| | | KI06 | | KI07 | | Fluconazole | Voriconazole | Pasaconazole |
|---|---|---|---|---|---|---|---|---|
| Species | Isolate | 50% | 100% | 50% | 100% | 50% | 100% | 100% |
| A. fumigatus | AF1 | 8 | 8 | 4 | 4 | — | 1 | — |
| | AF2 | 32 | 32 | 16 | >64 | — | 8 | — |
| | AF3 | 8 | 16 | 8 | 8 | — | 4 | — |
| Fusarium | FO1 | 8 | 8 | 8 | 8 | — | >16 | — |
| | FO2 | 4 | 8 | 4 | 4 | — | >16 | — |
| | FS1 | 4 | 8 | 4 | 4 | — | >16 | — |
| L. prolificans | LP1 | 2 | 2 | 2 | 2 | — | >16 | — |
| Scedosporium | SA1 | 2 | 4 | 1 | 2 | — | 1 | — |
| | SB1 | 1 | 8 | 1 | 2 | — | 2 | — |
| Apophysomyces | APO1 | 2 | 2 | 4 | 8 | — | — | 0.125 |
| | APO2 | 1 | 4 | 4 | 8 | — | — | 0.125 |
| | APO3 | 1 | 4 | 4 | 4 | — | — | 0.25 |

CLSI M27 & M38 methodologies were used to measure MICs
☐ All testing performed in RPMI buffered with 0.165M MOPS
☐ Concentration range for KI06, KI07, and Fluconazole: 0.125-64 mcg/ml
☐ Concentration range of Voriconazole and Posaconazole: 0.03-16 mcg/ml
☐ MICs at 24-72 hours
☐ Candida auris DI17-46 = isolate used in murine model
All values mcg/ml Antifungal activity for various compounds against a various B. dermatitidis isolates is illustrated in Table 4.

TABLE 4

Minimum inhibitory concentrations of compounds against various B. dermatitidis isolates

| | | KI07 | | KI07 | | Voriconazole |
|---|---|---|---|---|---|---|
| Species | Isolate | 50% | 100% | 50% | 100% | 100% |
| B. dermatitidis | BD1 | 2 | 4 | 2 | 4 | 0.06 |
| | BD2 | 4 | 4 | 4 | 4 | ≤0.03 |
| | BD3 | 2 | 4 | 2 | 2 | 0.125 |

CLSI M27 & M38 methodologies were used to measure MICs
☐ All testing performed in RPMI buffered with 0.165M MOPS
☐ Concentration range for KI06, KI07, and Fluconazole: 0.125-64 mcg/ml
☐ Concentration range of Voriconazole and Posaconazole: 0.03-16 mcg/ml
☐ MICs at 24-72 hours
☐ Candida auris DI17-46 = isolate used in murine model
All values mcg/ml Antibacterial activity for various compounds against a variety of exemplary bacterial species is illustrated in Table 2.

TABLE 2

Minimum inhibitory concentration of compounds against bacterial strain[a]

| Compound | E. coli (25922) | S. aureus (ATCC 25923) | S. aureus (ATCC 33591) MRSA | S. aureus (ATCC 43300) MRSA |
|---|---|---|---|---|
| KI01 | >256 | >256 | >256 | >256 |
| KI02 | >256 | >256 | >256 | >256 |
| KI03 | >256 | >256 | >256 | >256 |
| KI04 | 32 | 32 | 128 | 128 |
| KI05 | 64 | 16 | 32 | 32 |
| KI06 | 32 | 16 | 16 | 16 |
| KI07 | 64 | 32 | 32 | 32 |
| KI08 | >256 | >256 | >256 | >256 |
| KI09 | 128 | 32 | 128 | 32 |
| KI10 | 128 | 128 | >256 | >256 |
| Neomycin | 2 | 2 | — | — |
| Vancomycin | — | — | 2 | 2 |

[a]Unit: μg/mL

General procedure for the synthesis of KI06 and KI07. 0.582 gm (1 equiv., 1 mmol) of kanamycin and 3 equiv. of potassium carbonate were dissolved in 10 mL of water; then 2 equiv. of NHS-acyl ester dissolved in 10 mL of DMF was added in 4 portions at one-hour intervals. After 48 hours of reaction, solvent was removed by air flow and the compound was purified by column chromatography using MeOH to 10% $NH_4OH$ in MeOH. These compounds were also converted to the cationic forms and chloride salts using IRA-410 (Cl⁻) or Dowex 1×8-200 (Cl⁻).

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art and are also intended to be encompassed by the following claims.

What is claimed is:

1. An amphiphilic kanamycin compound, or salt thereof, having the formula:

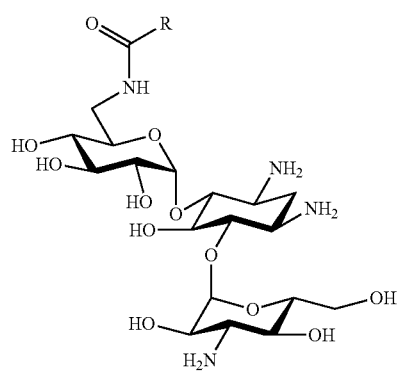

wherein R is an unsubstituted $C_{17}$-alkyl.

2. A method of synthesizing the amphiphilic kanamycin compound of claim 1, the method comprising:
reacting kanamycin sulfate having the formula:

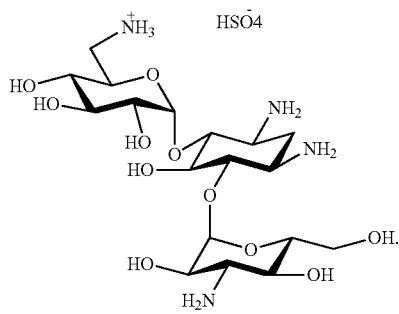

with $K_2CO_3$ and a compound having the formula:

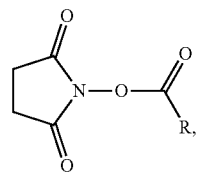

wherein R is an unsubstituted $C_{17}$-alkyl.

3. A method of treating an infection, the method comprising:
administering to a host in need thereof an effective amount of an amphiphilic kanamycin compound, or salt thereof, having the formula:

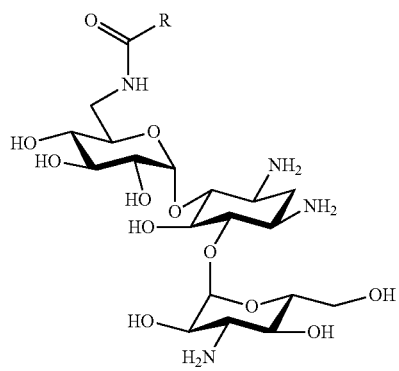

wherein R is an unsubstituted $C_{17}$-alkyl.

4. The method of claim 3, wherein the infection is a bacterial infection.

5. The method of claim 3, wherein the infection is a fungal infection.

6. The method of claim 3, wherein the infection is a fungal and bacterial infection.

* * * * *